US011039940B2

(12) United States Patent
Lunau et al.

(10) Patent No.: US 11,039,940 B2
(45) Date of Patent: Jun. 22, 2021

(54) MEASUREMENT AND ORDERING SYSTEM FOR ORTHOTIC DEVICES

(71) Applicant: VISION QUEST INDUSTRIES INCORPORATED, Irvine, CA (US)

(72) Inventors: Kevin R. Lunau, Valley Center, CA (US); Wallace R. Fischer, Amesville, OH (US); Michael S. Skahan, Ramona, CA (US)

(73) Assignee: VISION QUEST INDUSTRIES INCORPORATED, Irvine, CA (US)

( * ) Notice: Subject to any disclaimer, the term of this patent is extended or adjusted under 35 U.S.C. 154(b) by 192 days.

(21) Appl. No.: 16/404,580

(22) Filed: May 6, 2019

(65) Prior Publication Data
US 2019/0254842 A1   Aug. 22, 2019

Related U.S. Application Data

(63) Continuation of application No. 15/636,816, filed on Jun. 29, 2017, now Pat. No. 10,278,835.
(60) Provisional application No. 62/356,480, filed on Jun. 29, 2016.

(51) Int. Cl.
*A61F 2/50* (2006.01)
*A61F 5/01* (2006.01)
(Continued)

(52) U.S. Cl.
CPC .......... *A61F 2/5044* (2013.01); *A61F 5/0106* (2013.01); *A61F 5/0123* (2013.01);
(Continued)

(58) Field of Classification Search
CPC .... A61F 2/0106; A61F 2/5044; A61F 5/0106; A61F 5/0123; G16H 40/67; G16H 50/50
See application file for complete search history.

(56) References Cited

U.S. PATENT DOCUMENTS

| 7,643,893 B2 | 1/2010 | Troy et al. |
| 8,417,109 B2 | 4/2013 | Takatsuka et al. |

(Continued)

OTHER PUBLICATIONS

International Application No. PCT/US20/31306, International Search Report and the Written Opinion of the International Searching Authority, or the Declaration dated Aug. 3, 2020 (9 Pages).
(Continued)

*Primary Examiner* — Minh Q Phan
(74) *Attorney, Agent, or Firm* — Lawrence N. Ginsberg

(57) ABSTRACT

A system and method are provided for electronically capturing a subject's anatomy comprising an electronic device with a camera, display screen, and end-user software program to interface with the user. The software program tracks a target placed in view area, and gives visual feedback to the user based on target tracking. The software program includes criteria represented visually, via audio feedback, or haptic feedback, to the user indicating how to position the camera relative to the anatomy. The end-user software program may have means to automatically capture anatomy on the electronic device based on the criteria being met. The end-user software program may include an auto-zoom, target distortion correction features, and/or other features such as the use of a virtual markers.

15 Claims, 16 Drawing Sheets

(51) Int. Cl.
  *G16H 40/63* (2018.01)
  *G16H 40/67* (2018.01)
  *G16H 50/50* (2018.01)
  G16H 20/30 (2018.01)
  G16H 20/60 (2018.01)
(52) U.S. Cl.
  CPC ............ *G16H 40/63* (2018.01); *G16H 40/67* (2018.01); *G16H 50/50* (2018.01); *G16H 20/30* (2018.01); *G16H 20/60* (2018.01)

(56) References Cited

U.S. PATENT DOCUMENTS

| | | |
|---|---|---|
| 2007/0019942 A1 | 1/2007 | Kurosawa |
| 2015/0223730 A1 | 8/2015 | Ferrantelli |
| 2015/0271588 A1 | 9/2015 | Burgett et al. |
| 2016/0101571 A1 | 4/2016 | Schouwenburg et al. |
| 2019/0035149 A1 | 1/2019 | Chen et al. |
| 2020/0178651 A1* | 6/2020 | Hei ................. G06T 7/521 |

OTHER PUBLICATIONS

VQ Orthocare, eCast™ Custom Brace Instruction Manual, 2015 (12 Pages).

ossur.com, Smart Measure, from https://www.ossur.com/prosthetic-solutions/education-support/prosthetic-product-certifications/pro-flex-product-certification/2-uncategorised/1502-smart-measure-test, downloaded Jan. 4, 2018 (3 Pages).

PCT Application No. PCT/US2017/39879, Notification of Transmittal of the International Search Report and the Written Opinion of the International Searching Authority, or the Declaration dated Aug. 28, 2017 (9 Pages).

\* cited by examiner

MEASUREMENT AND ORDERING SYSTEM FOR ORTHOTIC DEVICES

CROSS REFERENCE TO RELATED APPLICATIONS

This patent application is a continuation-in-part of U.S. patent application Ser. No. 15/636,816 filed Jun. 29, 2017, entitled MEASUREMENT AND ORDERING SYSTEM FOR ORTHOTIC DEVICES.

This patent application claims the benefit of U.S. Provisional Application. No. 62/356,480 filed Jun. 29, 2016, entitled MEASUREMENT AND ORDERING SYSTEM FOR ORTHOTIC DEVICES. The entire contents of Application No. 62/356,480 and Ser. No. 15/636,816 are incorporated by reference herein.

BACKGROUND OF THE INVENTION

1. Field of the Invention

The present invention relates generally to the measurement of a subject's anatomy. An example is when measurements need to be taken of the anatomy to build a custom orthotic device tailored to the specific patient's anatomy. The present invention discloses a novel, convenient, electronic means to measure the anatomy.

2. Description of the Related Art

The most commonly practiced methods of measuring a patient's anatomy include casting, manual measurements, measuring devices, and digitizing the anatomy.

The first method of casting involves pre-marking landmarks on the patient's anatomy, for example the knee-center when casting the leg. Then the anatomy is cast with cast tape, allowing the markings to transfer to the inner surface of the cast tape. The cast tape hardens, and is cut off. The empty cast shell is then shipped to the custom brace manufacturer who then fills the cast with plaster, and cuts the cast away to gain a "positive" representation of the patient's leg with landmarks. As can be imagined, this gives an intimate and detailed model of the patient's anatomy, but is a slow, cumbersome, and expensive process.

Another method involves manually measuring one or more locations on the patient's anatomy, then recording and sending the information to the custom brace manufacturer. This is a much more straightforward process, but with the large disadvantage of omitting much of the patient's anatomical curves and contours. This could lead to an ill-fitting custom brace which has a higher likelihood of being rejected by the patient.

Another method involves the patient being physically present during the building process. This is of course the ideal scenario for the best-fitting brace, but is usually not feasible due to geographical and schedule limitations.

Still another method involves using a 3-dimensional scanning system to capture the entire leg anatomy. The major disadvantage of a full 3D digitizing setup is the cost and complication of the system.

There has been a partial response to these problems. U.S. Pat. Publication. No. US 2014/0063220 A1, issued to Taylor, entitled, "Method and Device for Ordering a Custom Orthopedic Device," discloses a method and device for digital measuring and ordering a custom orthopedic device.

An alternate embodiment is described in Taylor that deals with the generation of a three-dimensional model. Markers are added to the anatomy, but only to act as "dumb" reference points for generating the three-dimensional model from multiple views of the anatomy. Taylor does not teach about a smart target that is interpreted and tracked by the software on the fly, to determine distance and position of the camera relative to the anatomy, and to give real-time feedback to the user about how to correct the camera position in order to capture a well-oriented photo of the anatomy. Rather, the markers are used passively to construct a 3D model.

Another embodiment in Taylor includes depth of field measurements from the camera to determine position of anatomy. This is a different method of using the focus and zoom of the camera to determine the size of the anatomy in the display view area. The embodiment does not disclose anything regarding target patterns used in a real-time augmented reality scenario as the present invention uses.

SUMMARY OF THE INVENTION

In one embodiment the present invention is a system for electronically capturing a subject's anatomy, which involves using an auto-zoom feature and a target pattern. The system includes an electronic device and at least one target pattern. The electronic device includes: i) a camera configured to capture a subject's anatomical information of the anatomy of a subject; ii) a display screen; and, iii) an end-user software program configured to interface with a user via the display screen and to process information captured on the camera. The target pattern is for physical placement on the subject's anatomy.

The end-user program includes a user interface to provide user control of software functions. Software programming recognizes the target pattern in a view area of the camera. The software programming utilizes an auto-zoom feature to zoom in to the target pattern to provide a close-up of the target pattern, verify the target pattern, then zoom out to provide proper framing of the anatomy. The auto-zoom feature is utilized while maintaining a substantially fixed camera distance from the subject. The software program provides feedback to the user based on the size, shape, or position of the at least one target pattern, for directing the user to move the camera appropriately relative to the target pattern, thereby resulting in an optimized view of said anatomical information. The software program also captures the optimized view of the anatomical information via the camera.

In another embodiment the system for electronically capturing a subject's anatomy includes an auto-zoom feature and a distortion correction feature. This system, like the previous embodiment, includes an electronic device and at least one target pattern. The electronic device includes: i) a camera configured to capture a subject's anatomical information of the anatomy of a subject; ii) a display screen; and, iii) an end-user software program configured to interface with a user via the display screen and to process information captured on the camera. The target pattern is for physical placement on the subject's anatomy.

The end-user program includes a user interface to provide user control of software functions. Software programming recognizes the target pattern in a view area of the camera. The software programming utilizes an auto-zoom feature to zoom in to the target pattern to provide a close-up of the target pattern, verify the target pattern, then zoom out to provide proper framing of the anatomy. The auto-zoom feature is utilized while maintaining a substantially fixed camera distance from the subject. The software programming corrects distortions, if any, in the target pattern. It calculates an optimal vector from an origin on the target pattern positioned on the subject's anatomy, the optimal vector being normal to the surface of an undistorted target pattern. An actual vector is calculated from the origin of the target pattern to the camera. Using the difference between the optimal vector and the actual vector, an image collected by the camera is corrected to what it would be if the camera was actually positioned on the optimal vector, resulting in an optimized view of the anatomical information. The software programming also captures the optimized view of the anatomical information via the camera.

In another embodiment the system for electronically capturing a subject's anatomy includes a distortion correction feature, a target pattern, but without an auto-zoom feature. This system, like the previous embodiment, includes an electronic device and at least one target pattern. In this embodiment, the end-user program includes a user interface to provide user control of software functions. Software programming recognizes the target pattern in a view area of the camera. The software programming corrects distortions, if any, in the target pattern. It calculates an optimal vector from an origin on the target pattern positioned on the subject's anatomy, the optimal vector being normal to the surface of an undistorted target pattern. The software programming directs the user to back the camera away from the anatomy to frame the image. It also provides feedback to the user for the purpose of directing the user to move the camera appropriately relative to the target pattern physically placed on the subject, thereby resulting in an optimized view of the anatomical information. The software programming also captures the optimized view of the anatomical information via the camera.

In another embodiment the system for electronically capturing a subject's anatomy includes an auto-zoom feature, with virtual markers, where the software identifies the anatomy of the subject. The end-user program includes a user interface to provide user control of software functions. The software programming directs the user to position the camera to recognize a subject's anatomy within the display screen. It uses the anatomical features of the recognized subject's anatomy, and the patient data entered by the user and known anthropometric data to estimate the optimal position of virtual markers. The software programming also places the virtual markers on an image presented to the user on the display screen at the estimated optimal position. It utilizes an auto-zoom feature and the virtual markers to zoom in to provide proper framing of the anatomy. The auto-zoom feature is utilized while maintaining a substantially fixed camera distance from the subject. The software programming provides feedback to the user based on the anatomical features for directing the user to move the camera appropriately relative to the virtual markers, thereby resulting in an optimized view of the anatomical information. Lastly, the software program captures the optimized view of the anatomical information via the camera to provide output data.

In another embodiment the system for electronically capturing a subject's anatomy includes an auto-zoom feature, with virtual markers, where the user identifies the anatomy of the subject. The end-user program includes a user interface to provide user control of software functions. The end-user software program directs the user to position the camera to frame the subject's anatomy within the display screen. It provides the user with a means to identify anatomical features of the subject's anatomy and direct the user to identify the anatomical features. It also places a virtual marker on an image presented to the user on the display screen. The software program utilizes an auto-zoom feature and the virtual marker to zoom in to provide proper framing of the anatomy. The auto-zoom feature is utilized while maintaining a substantially fixed camera distance from the subject. Feedback is provided to the user based on the anatomical features for directing the user to move the camera appropriately relative to the virtual marker, thereby resulting in an optimized view of said anatomical information. The software program captures the optimized view of the anatomical information via the camera.

Thus, in embodiments, the system includes a unique series of features to allow accurate and convenient measurement of the anatomy via a camera, an electronic device with an associated end-user software program installed, and a specific target area that the pattern recognition software embedded in the end-user software program recognizes.

The target pattern(s) is/are a known size and shape programmed into the end-user software program.

The pattern recognition function of the end-user software scans the image in real time for the target pattern and places feedback markers on the display based on the embedded target parameters. These feedback markers guide the user to orient the camera such that relationship to the anatomy is correct for measurement. When the software program determines the camera is correctly placed, it can automatically capture an image or video of the anatomy.

In another broad aspect, the edge detection software function can scan for and detect anatomic edges (i.e. anatomic contours) and determine if the anatomy is fully displayed, or whether it may be blocked or incomplete.

For example, the subject's clothing may be obstructing a portion of the anatomy. If this is the case, the edge detection function of the end-user software program will alert the system user to address the issue before capturing the anatomical data.

The end-user software program also includes a software positioning function that can check for proper position and shape of the anatomy (as opposed to orientation of the camera). For example, the software positioning function can check for proper flexion in the lateral (side) view of the leg. If the leg is in too much flexion, the end-user software program can alert the user.

Other objects, advantages, and novel features will become apparent from the following detailed description of the invention when considered in conjunction with the accompanying drawings.

BRIEF DESCRIPTION OF THE DRAWINGS

FIG. 9A shows target recognition. FIG. 9B shows a target pattern verification by zooming into the target pattern. FIG. 9C shows an auto-zoom out to provide a proper framing of the anatomy. FIG. 9D illustrates user instructions to move the camera to properly align with the anatomy. FIGS. 9E-9H illustrate repeating this process using a lateral (side) view.

FIGS. 12A and 12B illustrate software recognition of the anatomy of the subject. FIG. 12C illustrates the system placing the virtual markers on the display screen. FIG. 12D illustrates user correction capability. FIG. 12E illustrates the auto-zoom feature and the virtual markers zoomed in to provide proper framing of the anatomy. FIG. 12F illustrates the capture of the optimized.

DETAILED DESCRIPTION OF THE INVENTION

Figure 1:
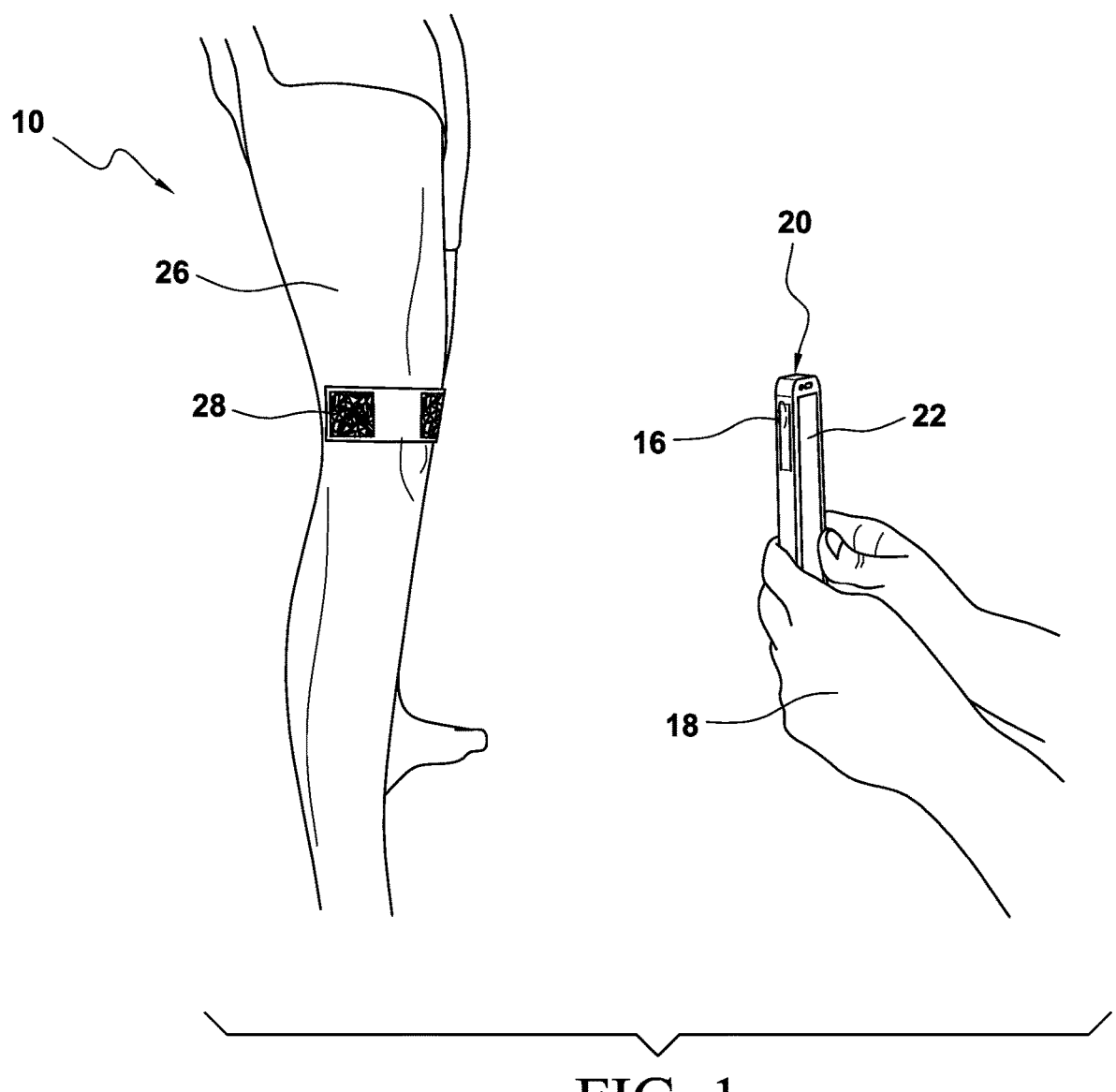
FIG. 1 is a general view of the system of the present invention, and anatomy of the user.

Referring now to the drawings and the characters of reference marked thereon, FIG. 1 illustrates the system of the present invention, designated generally as 10. The user 18 places tape 28 on the anatomy 26. The user 18 then positions electronic device 20 which includes camera 16, to capture the anatomical information 26.

Figure 2:
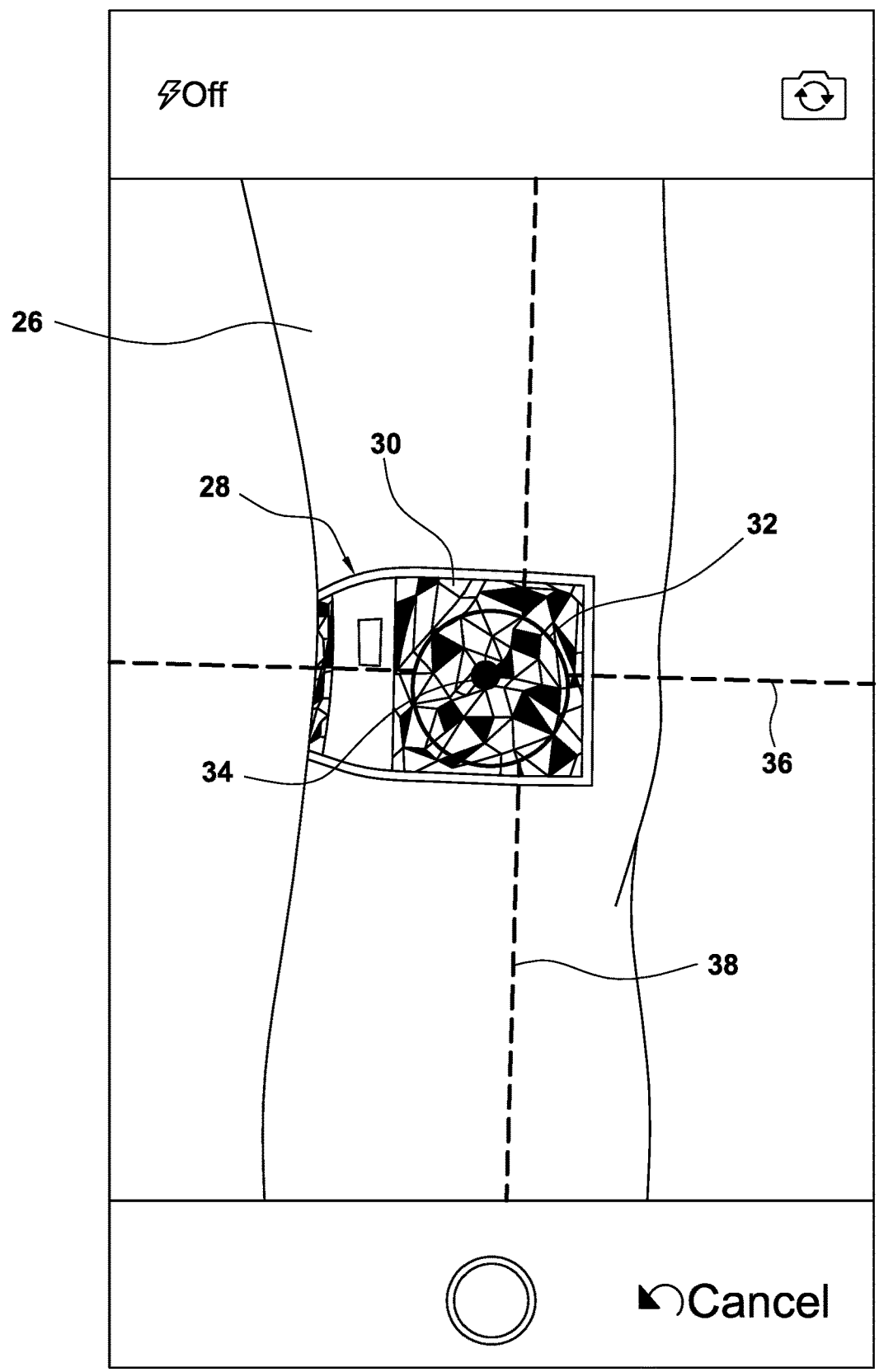
FIG. 2 shows the display screen with an anterior (front) view of the anatomy, the target pattern, and feedback markers.

Referring now to FIG. 2, tape 28 is applied to the anatomy. An end-user software program installed on electronic device 20 is used to recognize the size, shape, or position of at least one target pattern 30 on tape 28. The electronic device program finds the target pattern 30 and uses it to provide feedback to the user for the purpose of directing the user 18 to move the camera 16 to result in an optimized view of the anatomical information 26. One way to give feedback is to place feedback markers on display 22 for the user 18 to orient the camera 16. These feedback markers guide the user 18 to re-orient the camera 16 until it is in a suitable or optimized position to capture the anatomy 26.

Examples of feedback markers for an anterior (front) view include several display items which can act independently, or in conjunction with one another. One type of feedback marker could be a pitch line 36, which guides the user to position the camera at the correct pitch angle (i.e. pivoting about an axis parallel to the intersection of coronal and transverse planes). Still another feedback marker could be a yaw line 38, which guides the user to position the camera at the correct yaw angle (i.e. pivoting about an axis parallel to the intersection of coronal and sagittal planes).

The pitch line 36 and yaw line 38 together guide the user to position the camera at the correct roll angle (i.e. pivoting about an axis parallel to the intersection of the transverse and sagittal planes).

Figure 3:
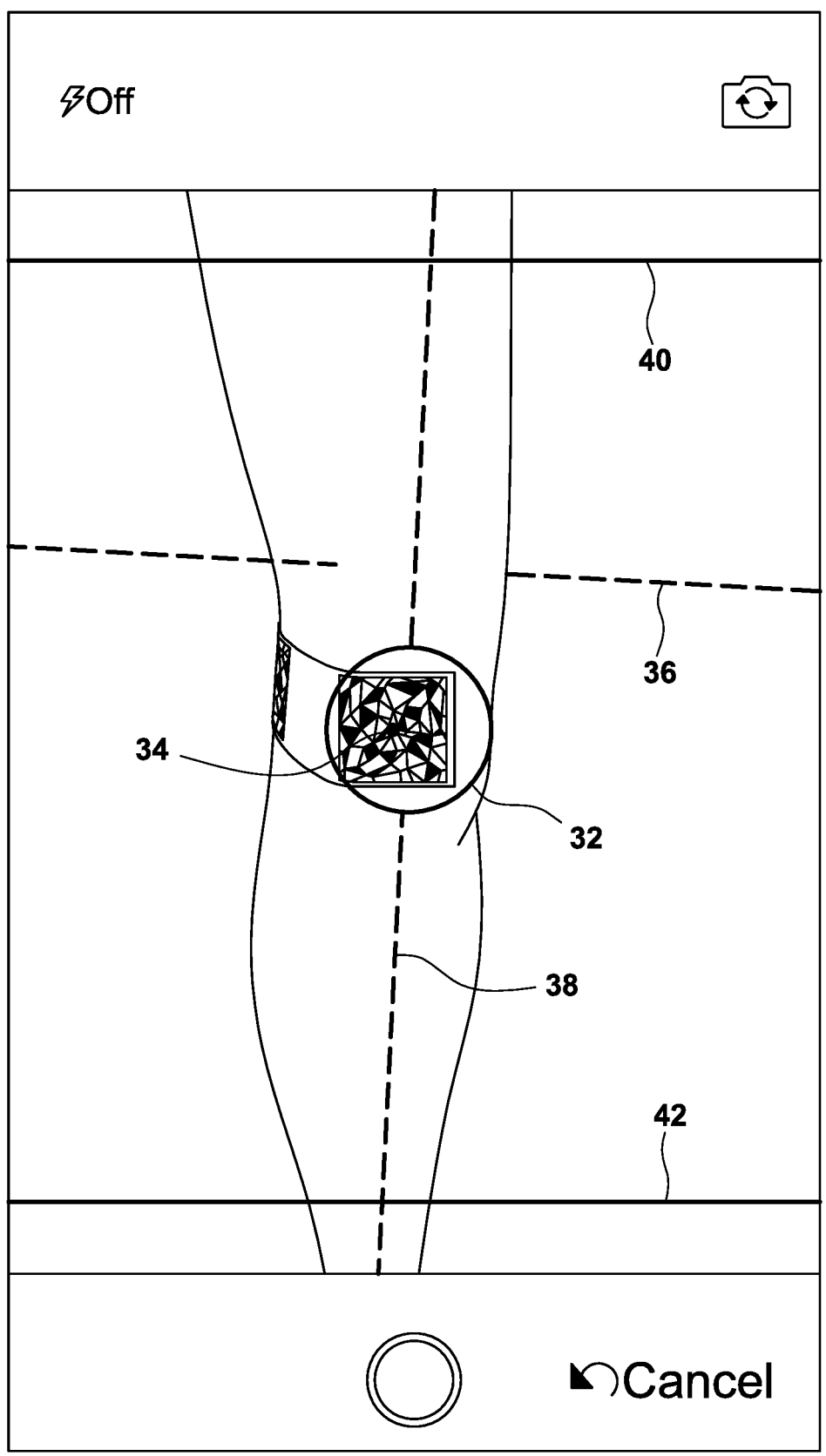
FIG. 3 shows the display screen with an anterior (front) view of the anatomy, showing a feedback marker that needs correction.

Referring now to FIG. 3, another type of feedback marker could be a center zone 32, which is used to guide the user to move the camera to the correct position in the coronal plane (up, down, left, right in the coronal plane). Still another feedback marker could be top distance line 40 and bottom distance line 42. These lines give the user feedback as to how far back the camera needs to be placed (movement perpendicular to the coronal plane) in order to capture enough of the anatomy for proper measurement.

A visual technique to communicate this to the user is by the use of position and color on the display 22. One or all of the above markers can change attributes, (such as size, position, or color) on display 22 to give the user feedback on how to correct the camera position or angle and capture the anatomy 26 properly.

For example, the feedback markers can turn red if they need correction, and they can move along the display 22 in real-time to alert the user which way to re-orient the camera to correct the position. FIG. 2 shows a mostly correctly-positioned camera: pitch line 36, yaw line 38, center marker 34 are all green and in the correct position. However, top distance line 40 and bottom distance line 42 are not shown on the screen, indicating the camera is too close to the anatomy.

Now referring to FIG. 3, the top distance line 40 and bottom distance line 42 are shown, and colored green, for example. These top/bottom distance lines 40, 42 are controlled by the end-user software program based on the known size, shape, or position of the target pattern 30. The program scans target pattern 30 as the camera 16 is moved perpendicular to the coronal plane, and re-positions/re-colors, or changes attributes of these lines 40, 42 accordingly, based on the relative size, shape, or position of the target pattern 30. As the camera 16 is moved away from the anatomy 26, the target pattern 30 becomes smaller and lines 40, 42 are moved closer together. As the camera is moved closer to the anatomy, the lines 40, 42 are moved further apart. If the target pattern 30 is within a predetermined size range (based on distance of camera from anatomy), the lines 40, 42 are colored green. If the camera is too far away from the anatomy, the lines 40, 42 are colored red. If the camera is too close, the lines 40, 42 are not displayed. In either case, the end-user software program will not allow the anatomy to be captured.

In FIG. 3 for example, all other feedback markers are colored green, except the red pitch line 36. The pitch line 36 is red and is shown above the knee center marker 34, which means the camera is tilted (pitched) too low. A software function embedded in the end-user software program can use data from a sensor in the electronic device to determine whether the camera is tilted too high or too low. If the camera is tilted beyond pre-set angle limits, the pitch line 36 is colored red for example, and re-positioned on the display 22 according to the degree of improper tilt, to alert the user to correct the pitch angle. If the camera is tilted too far down, the pitch line 36 will be turned red and moved up on the display 22, out of range. If the camera is tilted too far up, the pitch line 36 will be turned red and moved down, out of range.

Similarly, the yaw line 38 is linked to the relative shape of the target pattern 30. If the displayed target shape deviates too much from the pattern recognition software's predefined shape, the yaw line 38 will move accordingly and become red, preventing the anatomical data from being captured.

Figure 4:
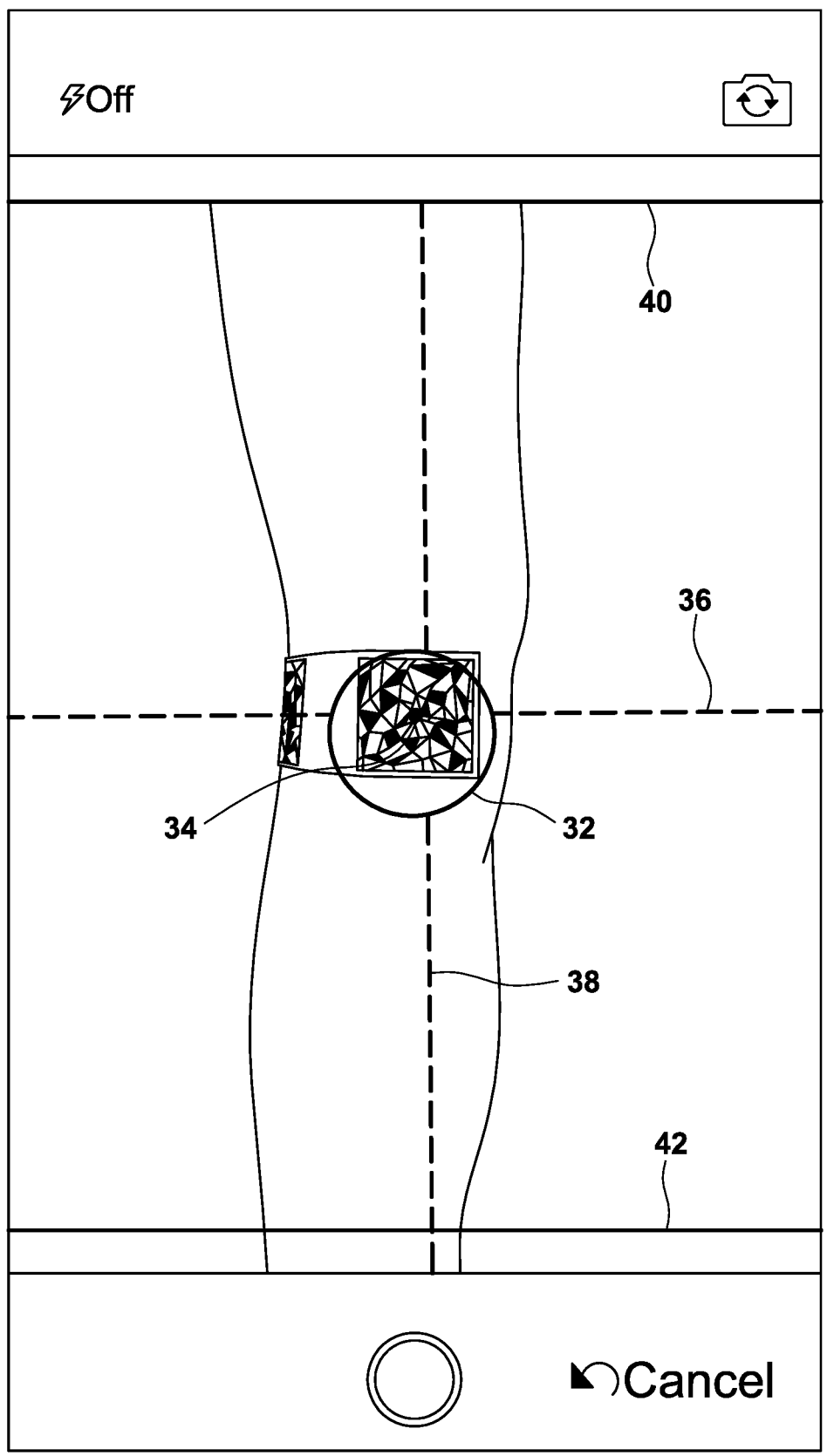
FIG. 4 shows the feedback markers with the orientation corrected.

Now referring to FIG. 4, all feedback markers are green, so the camera is in the correct position for capturing the data that described the anatomy 26. The feedback markers are visual displays, or auditory or haptic feedback cues to the user, and are driven by predefined criteria in the end-user software program of what constitutes a well-defined or optimized anatomical view. Once the predefined criteria is met, the program can allow the camera to automatically capture the anatomy 26 by taking a photograph or video of the anatomy 26, along with some or all of the feedback markers or other data or metadata such as electronic measurement information. For example, the stored image could include just the center marker 34 and the top/bottom distance lines 40, 42.

Figure 5:
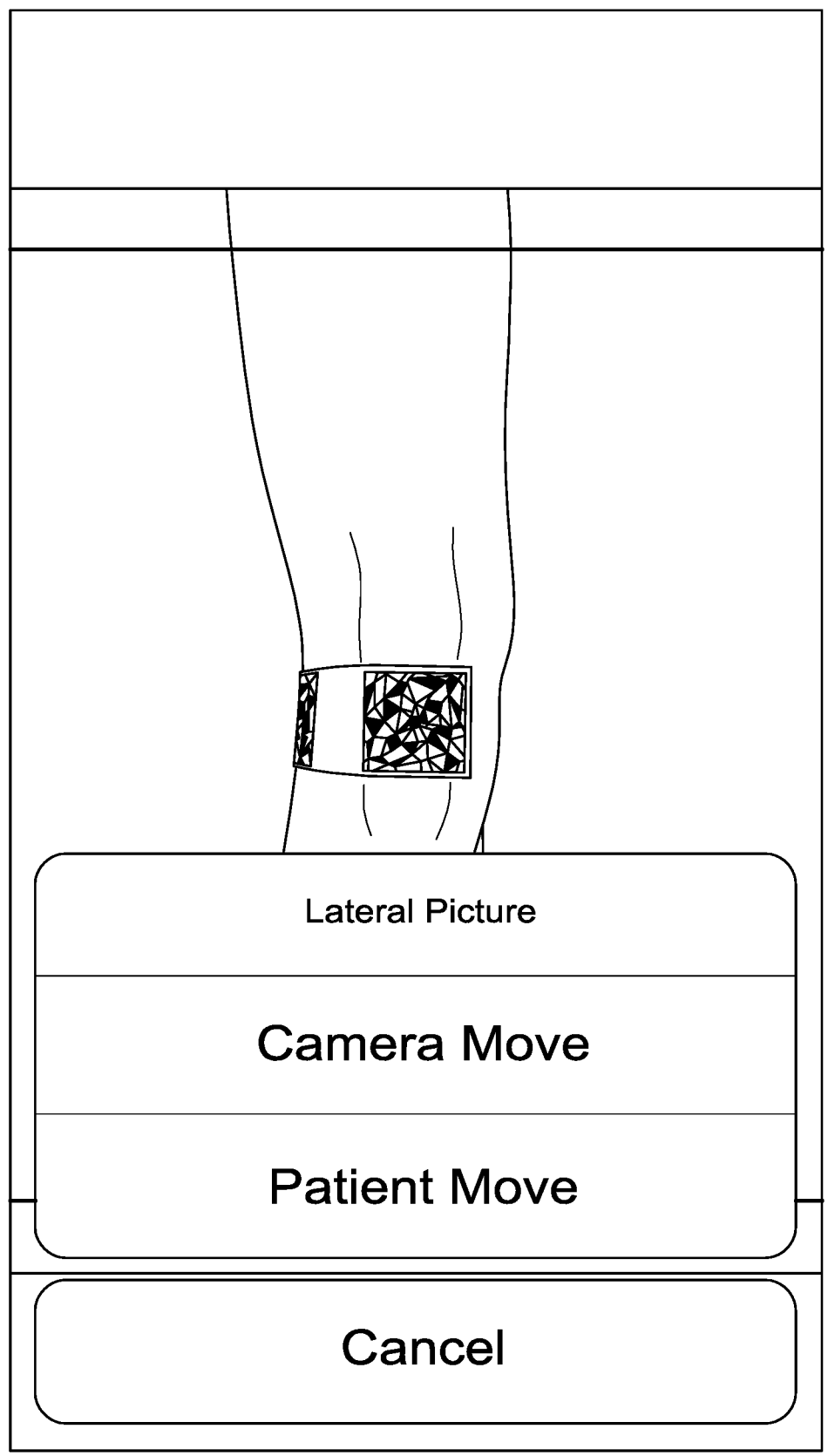
FIG. 5 shows a query screen asking the user to choose how to orient the next photo.

Referring now to FIG. 5, the successful anterior view is complete, and now the end-user software program queries the user to either move the camera or the patient to take a lateral (side) view.

Figure 6:
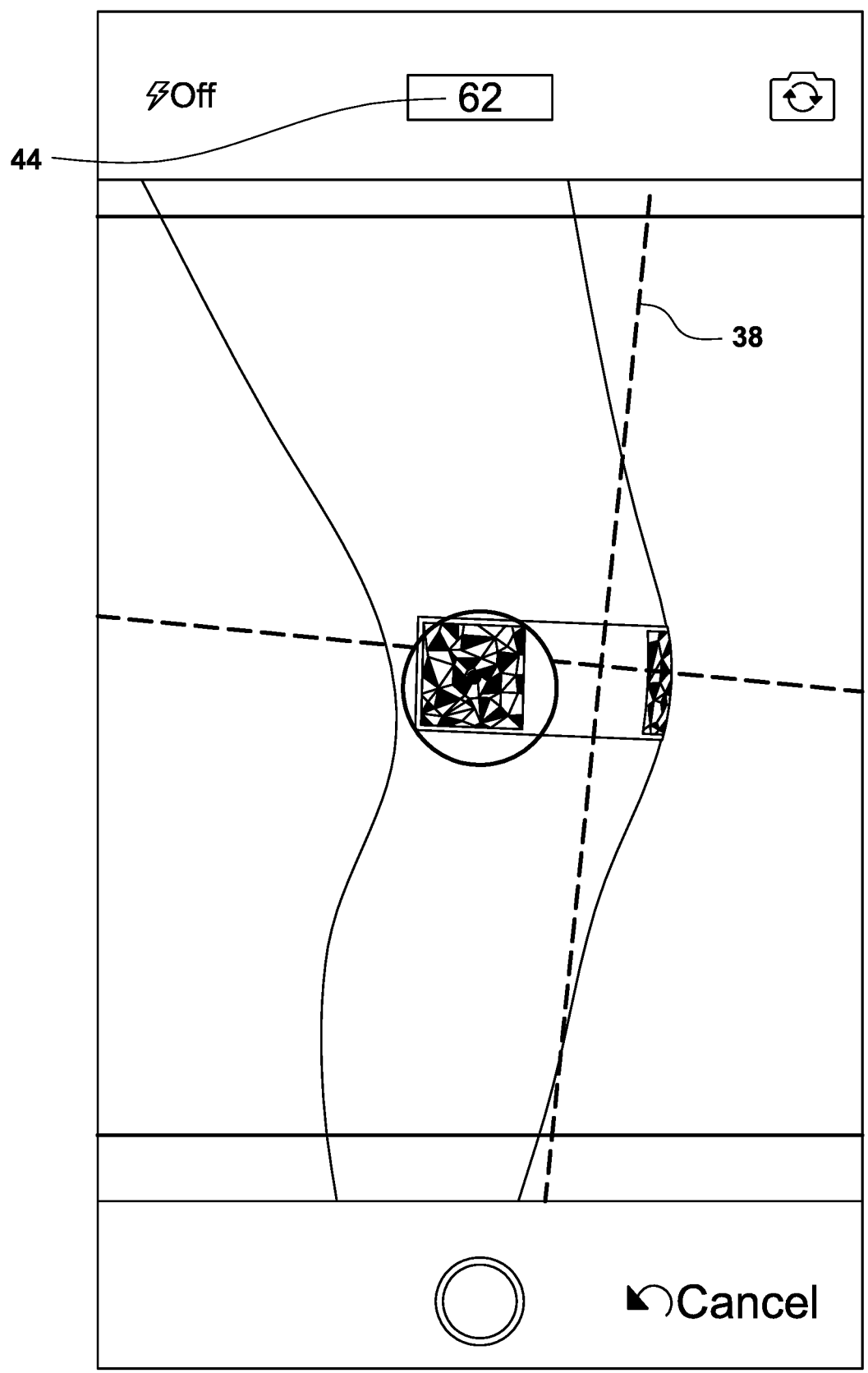
FIG. 6 shows the display screen with an lateral (side) view of the anatomy, showing a feedback marker that needs correction.

Referring to FIG. 6, if the camera is moved, the end-user software program stores the anterior view camera orientation via the on-board compass or other sensor, and displays another feedback marker of the lateral yaw angle 44. This guides the user to pivot the camera around to the lateral side of the anatomy, somewhere close to 90-degrees from where the anterior anatomy 26 was captured. FIG. 6 shows the lateral yaw angle 44 as 62-degrees, which is not within the tolerance to capture the lateral anatomy. Accordingly, the yaw line 38 is off-center and displayed in red, preventing the anatomy from being captured.

Figure 7:
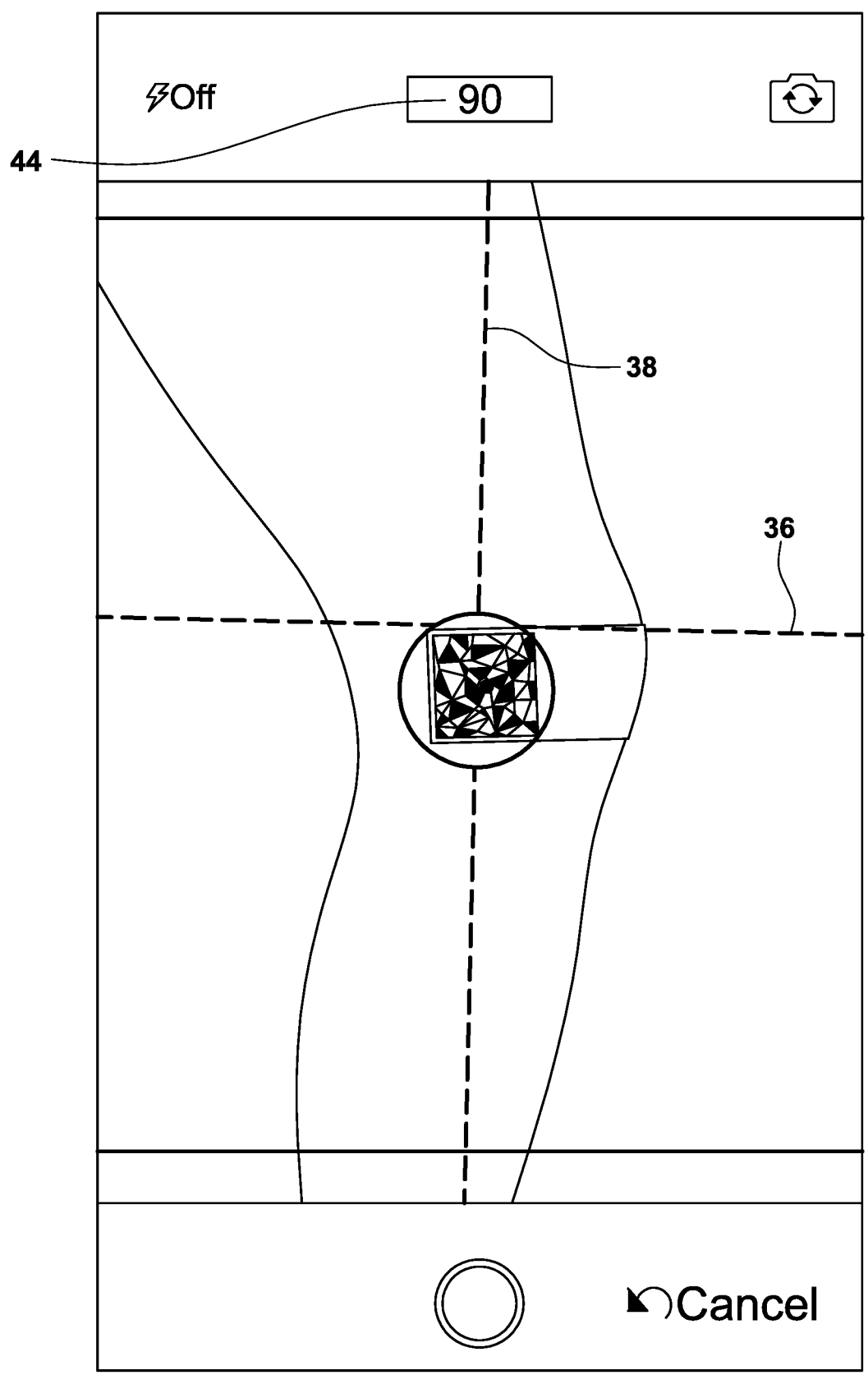
FIG. 7 shows the feedback markers with the orientation corrected.

FIG. 7, however, shows a lateral yaw angle of 90-degrees, which would allow the lateral anatomy to be captured. Of course, all other feedback markers described above (such as pitch line 36) are still active, assuring the camera will be correctly-oriented to the lateral anatomy.

Referring back to FIG. 5, the other option to capture lateral anatomy would be to choose "Patient Move". If this option is chosen, the end-user software program does not use the lateral yaw angle 44 since the patient is moving, not the camera.

The pattern recognition function of the end-user software program, combined with pre-defined criteria relative to known target pattern 30, correctly-oriented anatomy 26, and electronic measurement information such as feedback marker displays can all be stored with the captured photographs or videos. For example, relative to the target pattern in the anterior view of the anatomy, the pre-defined criteria as programmed in the software function, as measured by the sensors in the electronic device 20, and as shown on the display 22, are used to control and give feedback to the user 18 on the six basic degrees of freedom: yaw, pitch, roll angles, and linear movement normal to coronal, sagittal, and transverse planes. This can be translated to the camera's: pitch, yaw, roll, distance, height, or horizontal position, all relative to the target pattern.

The pattern recognition function of the end-user software program includes known size, shape, or position parameters of the target pattern 30. These known parameters of the target pattern are used as a baseline to extrapolate the size, shape, or position of the anatomical information into full-scale (i.e. actual size) measurements. This captured anatomical data and electronic measurement information can then be used to measure the anatomy 26 for various purposes. One such purpose is to build a custom orthotic device such as a custom knee brace.

The programming to use the known size, shape, or position parameters of the target pattern 30 to extrapolate the size, shape, or position of the anatomical information can exist on the electronic device 20, and/or on a remote device or system for further processing.

Note that the parameters can also be used to change the scale of the anatomy if desired. For example, this can be useful for post-operative patients that are anticipated to have muscle atrophy, or other recovering patients that are anticipated to have muscle hypertrophy. Different scaling can also be used to accommodate patients that are anticipated to gain or lose weight.

Scaling can be done isotropically (all axes equal), or anisotropically (axes have different scaling factors). Anisotropic scaling could be used to more closely mimic the anatomy changes for a particular purpose. For example, during weight loss, a thigh shrinks in girth, but not in length, so non-uniform scaling would give a better representation and corresponding fit.

Each of the electronic components (display 22, sensors, camera 16, etc.) can be remotely located, i.e. they need not be located on the same device.

Figure 8:
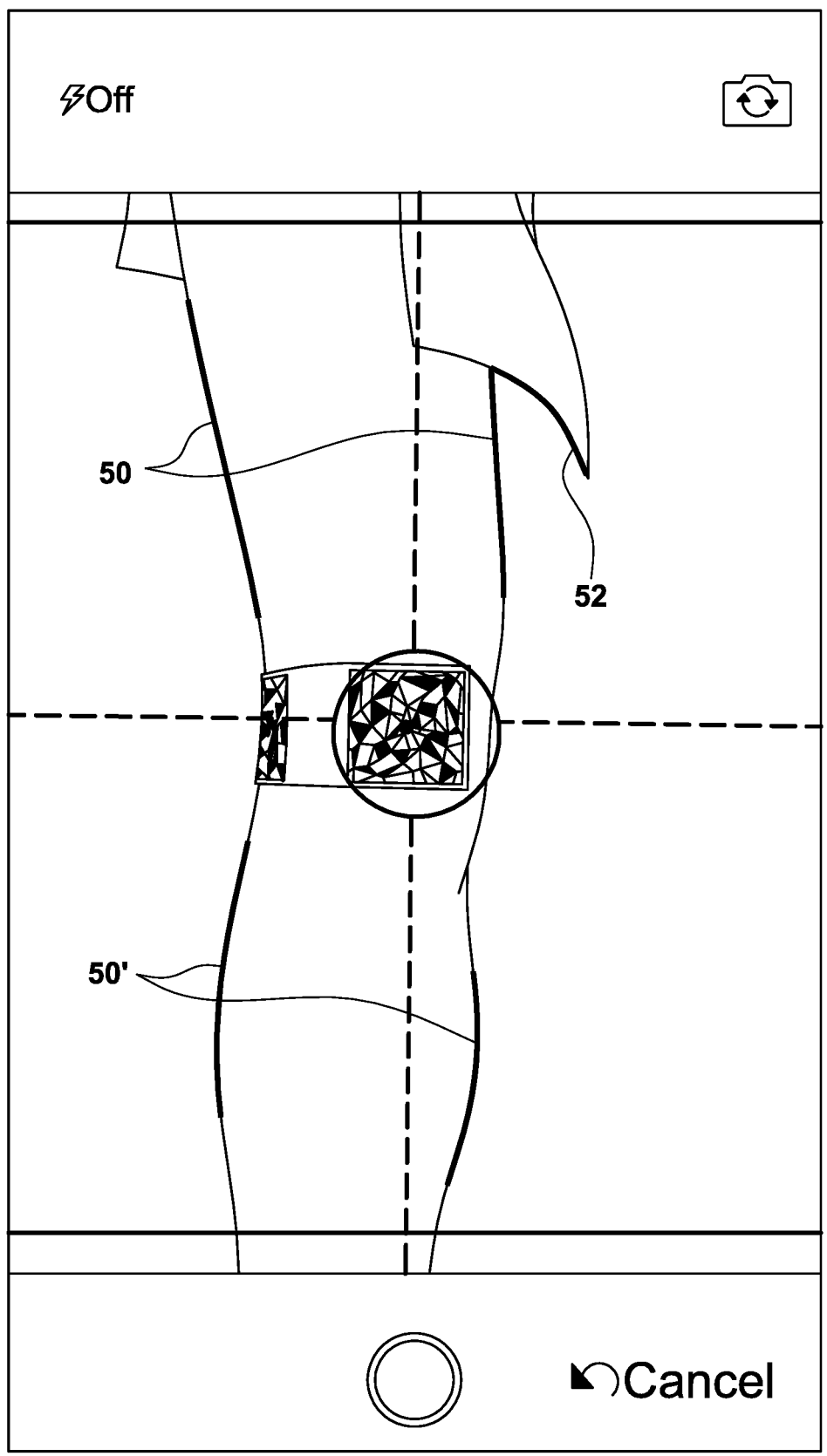
FIG. 8 is the display screen with an anterior (front) view of the anatomy, showing anatomic and non-anatomic contours.

In another embodiment, shown in FIG. 8, the edge recognition function of the end-user software program can be programmed to detect, distinguish, and analyze anatomic edges (i.e. anatomic contours) versus items in the background of the view. This edge detection functionality can be used to determine if the anatomy is correctly displayed prior to capture. For example, the function can scan for contrast, color, brightness, or other parameters denoting the edge of the anatomy. The software function can then trace the anatomy and the end-user software program may display an outline shape of the anatomy as anatomic edges or anatomic contours 50 and 50'.

If the edge detection function finds a discontinuity in the anatomic contours 50 and 50', it may display this as a non-anatomic contour 52. This may be displayed as a flashing line, or different colored line, or other change to alert the user. The non-anatomic contour 52 may be due to clothing or other item obscuring the anatomy, or may be due to the anatomy being in a non-ideal position, for example if the lateral view shows the leg in too much flexion, this would be undesirable for building a well-fitting custom brace.

There can be a provision to over-ride some or all of the above feedback markers and capture the anatomy anyway. There may also be a flag placed on the captured data/electronic measurement information to alert downstream users that an over-ride was used, and to be vigilant for less-than-ideal data. In some embodiments the system can instruct the user to tell the subject (patient) to reposition their anatomy or clothing. These features can likewise apply to the embodiments below. In some embodiments the system can offer the user a couple of choices on the screen to choose from, for example, referring to FIG. 8, on the medial side of the knee, the user can choose "Contour 50" or exclude "Contour 52" by touching the screen.

Once the anatomy has been captured, the end-user software program may have the means to transmit said captured information and other data to a remote server where it can be processed and used to build a custom orthotic device to fit said anatomy.

This system has the advantage that no physical measurements are taken by the user; all measurements are electronic, based on the size, shape or position of the target and associated programming, so they are easily performed, and quickly changed/repeated if necessary.

This invention has been discussed in relation to building custom orthotic devices, it may have other applications, such as building other custom fitted equipment including custom prosthetic devices, custom-fitted apparel, and custom exoskeletal devices. Furthermore, even though it has been shown in this patent application relative to its application to a knee, it may be used in many other applications, for example, but not limited to other parts of the anatomy such as feet, lower and upper leg, finger, wrist, hand, arm, shoulder, head, etc.

This invention has been discussed in relation to feedback that moves or changes color based on relative position of the camera and target pattern. Other means to provide feedback to the user are also feasible, such as via shapes or animation on display screen, audio signals, or haptic (sense of touch) feedback, or any combinations of the above.

This invention has been discussed using independent sets of measurements. Multiple measurements could be taken such as at the start and end of an activity that would allow comparison and contrast of positions. Study of movement or limitations of movement can be analyzed.

In an embodiment the electronic device is connectable to the internet, and the end-user software program is configured to transfer the optimized view of the anatomical information and electronic measurement information to a remote location.

As was discussed above, in an embodiment of the system of the present invention the image capturing device is moved in toward the target pattern to register the target pattern and then slowly moved away until the image of the anatomy is properly framed and captured. As was seen in FIGS. 3 and 4, the process of framing the image takes place when the top distance line 40 and bottom distance line 42 appear (red at first) and then turn green. When the top distance line 40 and the bottom distance line 42 are green the image in the view finder are adequately framed. This represents the establishment of a distance to the target pattern within a predetermined tolerance. The camera's view is limited to the area of the anatomy that will be used to finally achieve an optimized view.

Figure 9A:
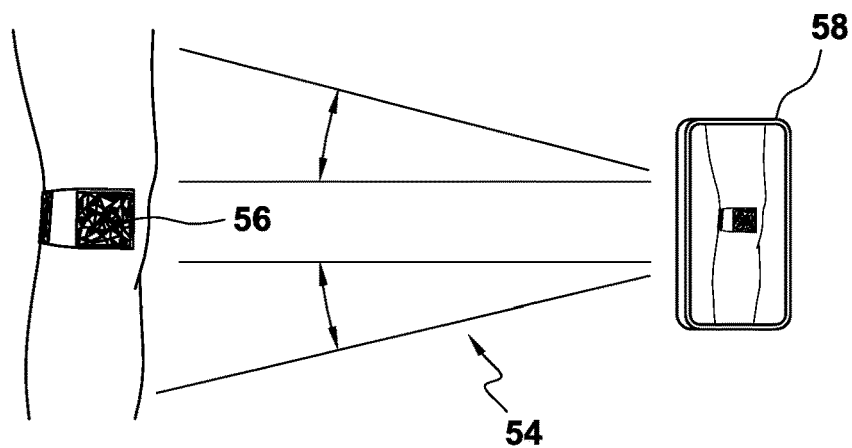
FIGS. 9A-H are schematic illustrations of an embodiment of a system for electronically capturing a subject's anatomy, utilizing an auto-zoom feature.
Figure 9B:
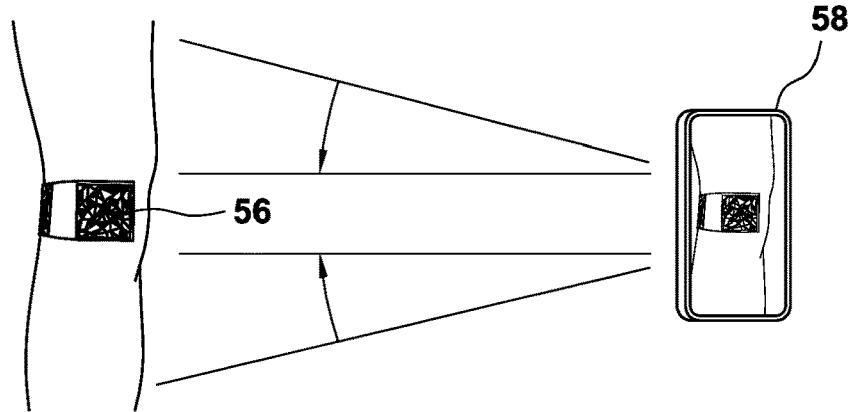
Figure 9C:
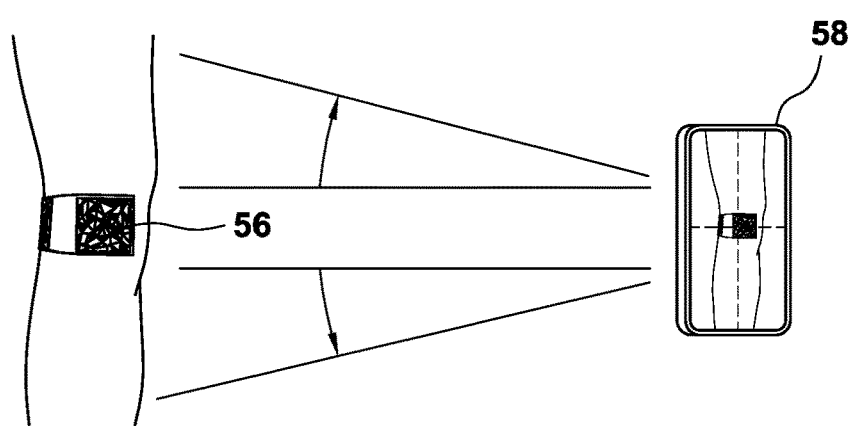

Referring now to FIGS. 9A-9H, in another embodiment, designated generally as 54, when initiating an image capture, a means of auto-zooming to frame the anatomy appropriately is utilized. In one auto-zoom embodiment a target pattern 56 is utilized. With the auto-zoom system 54 the end-user software is programmed to recognize the target pattern in a view area 58 of the camera, as shown in FIG. 9A. As shown in FIG. 9B, the software utilizes an auto-zoom feature to zoom in to the target pattern to provide a close-up 60 of the target pattern and verify the target pattern. As shown in FIG. 9C the auto-zoom feature then zooms out to broaden the view to provide proper framing of the anatomy for measurement. The auto-zoom feature, as shown in FIGS. 9A-9C is utilized while maintaining a substantially fixed camera distance from the subject. The auto-zoom feature can, for example, utilize the native functionality of the graphics processing unit of the camera making appropriate calls to the processor to achieve adequate zooming, as is known in the field and used in various applications, that are currently available.

Figure 9D:
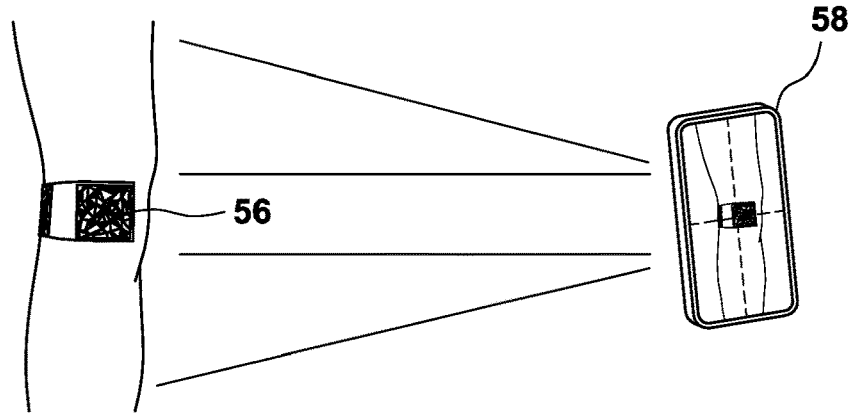
Figure 9E:
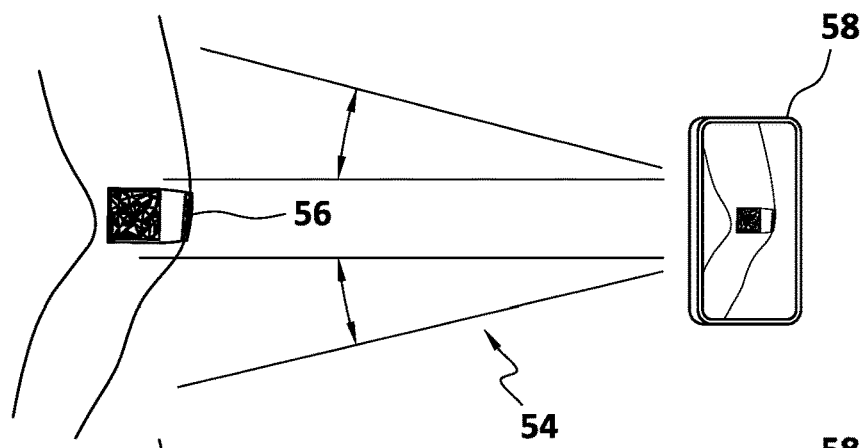
Figure 9F:
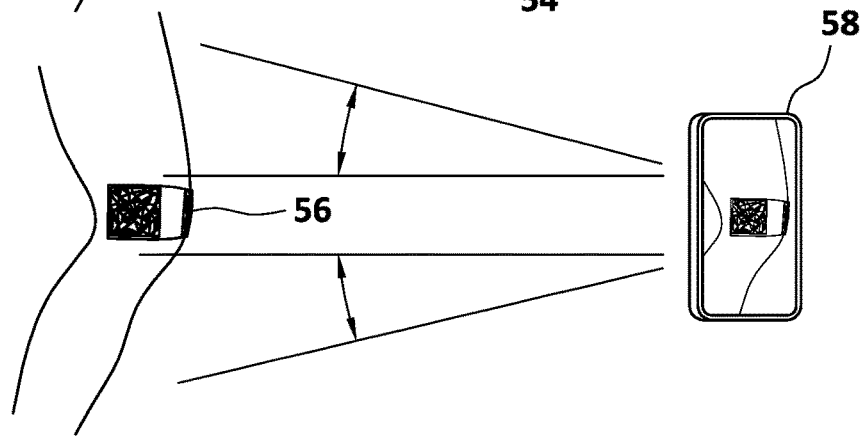
Figure 9G:
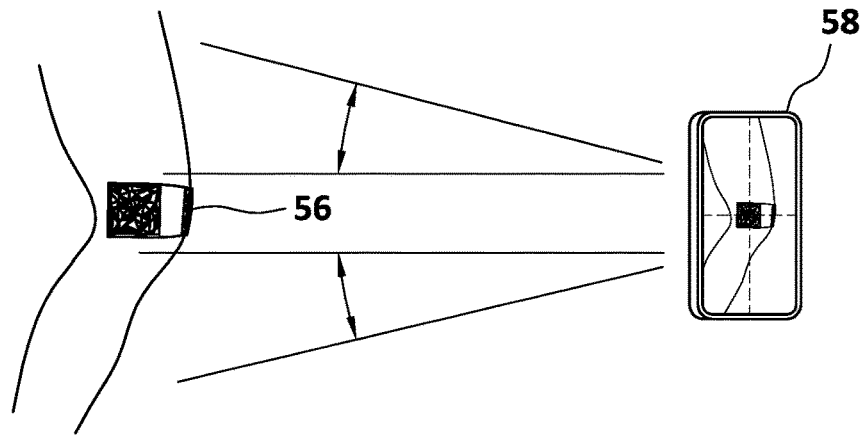
Figure 9H:
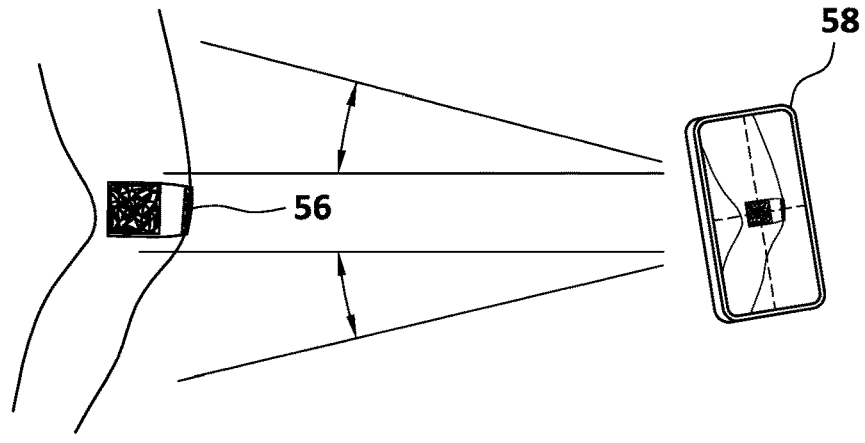

As shown in FIG. 9D, the user may then be directed (instructed) to move the camera to properly align with the anatomy. The user may be instructed to raise or lower the camera, shift the camera left or right, twist the camera right or left, or tip the camera forward or back. This movement of the camera optimizes the image.

A successful optimization of the image results in all feedback markers turning green and the image being automatically captured. The feedback markers include the top distance line, the bottom distance line, the pitch line, the yaw line, the center zone.

Referring now to FIGS. 9E-9H, the successful anterior view is complete, and now the end-user software program directs the user to either move the camera or the patient to take a lateral (side) view. The above steps are repeated for the lateral view process.

Thus, in summary, feedback is provided to the user based on the size, shape, or position of the target pattern. This feedback directs the user to move the camera appropriately relative to the target pattern, thereby resulting in an optimized view of the anatomical information. Such feedback can be, as discussed above, such as feedback markers, including, for example, pitch line, yaw line, center zone, various color related markers, etc.

As discussed above, the end-user software includes means to capture the optimized view of the anatomical information via the camera.

As discussed above, software programming extrapolates a known size, shape, or position of the target pattern into electronic measurements of the size, shape, or position of the anatomical information.

Figure 10A:
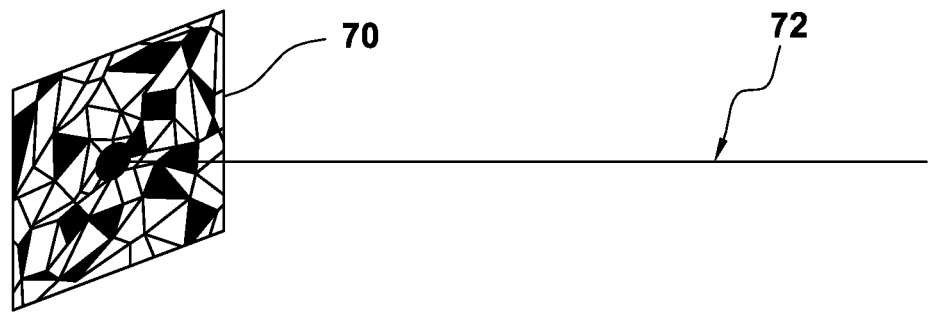
FIGS. 10A-B illustrate correction of the distorted target pattern utilizing the principles of the present invention.

When applying the target patterns to the anatomy, they are often distorted by the underlying anatomy. Referring now to FIG. 10A, use of an undistorted target pattern 70 provides an optimal vector 72. The optimal vector 72 is normal to the surface of an undistorted target pattern 70.

Figure 10B:
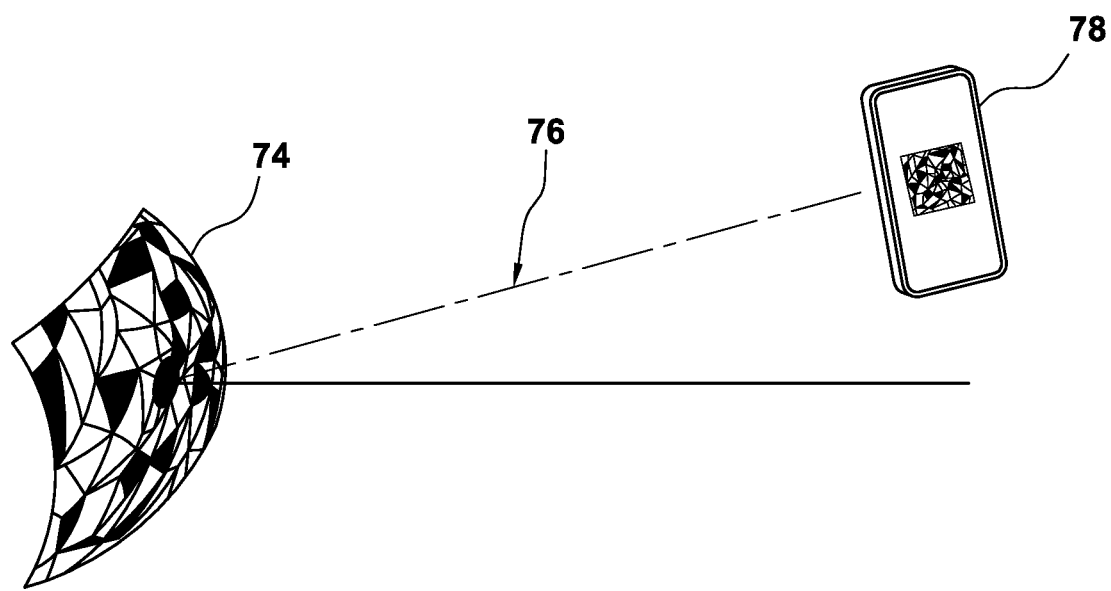

FIG. 10B illustrates use of a distorted target pattern 74. In this embodiment, the auto-zoom feature, discussed above, is combined with a means for correcting the distorted target pattern 74. The end-user software program includes software programming to recognize the target pattern, and use the auto-zoom feature mentioned above. The software programming corrects distortions, if any, in the target pattern. The distortions can be corrected utilizing image correcting algorithms that are known in the field, such as discussed in mathworks.com and available by Adobe Photoshop, GIMP, etc. Next, the optimal vector 72 is calculated. The optimal vector is calculated from an origin on the target pattern positioned on the subject's anatomy. An actual vector 76 is calculated from the origin of the target pattern 74 to the camera 78.

Using the difference between the optimal vector 72 and the actual vector 76, an image collected by the camera 78 is corrected to what it would be if the camera 78 was actually positioned on the optimal vector 72. This results in an optimized view of the anatomical information.

Then, as in the previous cases, the end-user program captures the optimized view of the anatomical information via the camera 78.

Thus, corrections can be made to compensate for distortions by the underlying anatomy as well as by the operator of the image capturing device being in a physically difficult position due to patient position, environmental challenges, or other contributing factors.

In summary, the FIG. 10A embodiment assumes an undistorted target pattern and the programming calculates an optimal vector from it. The FIG. 10B embodiment assumes that in many cases the target pattern is distorted by the underlying anatomy and programming is provided to correct for this distortion and more accurately calculate an optimal vector.

Figure 11:
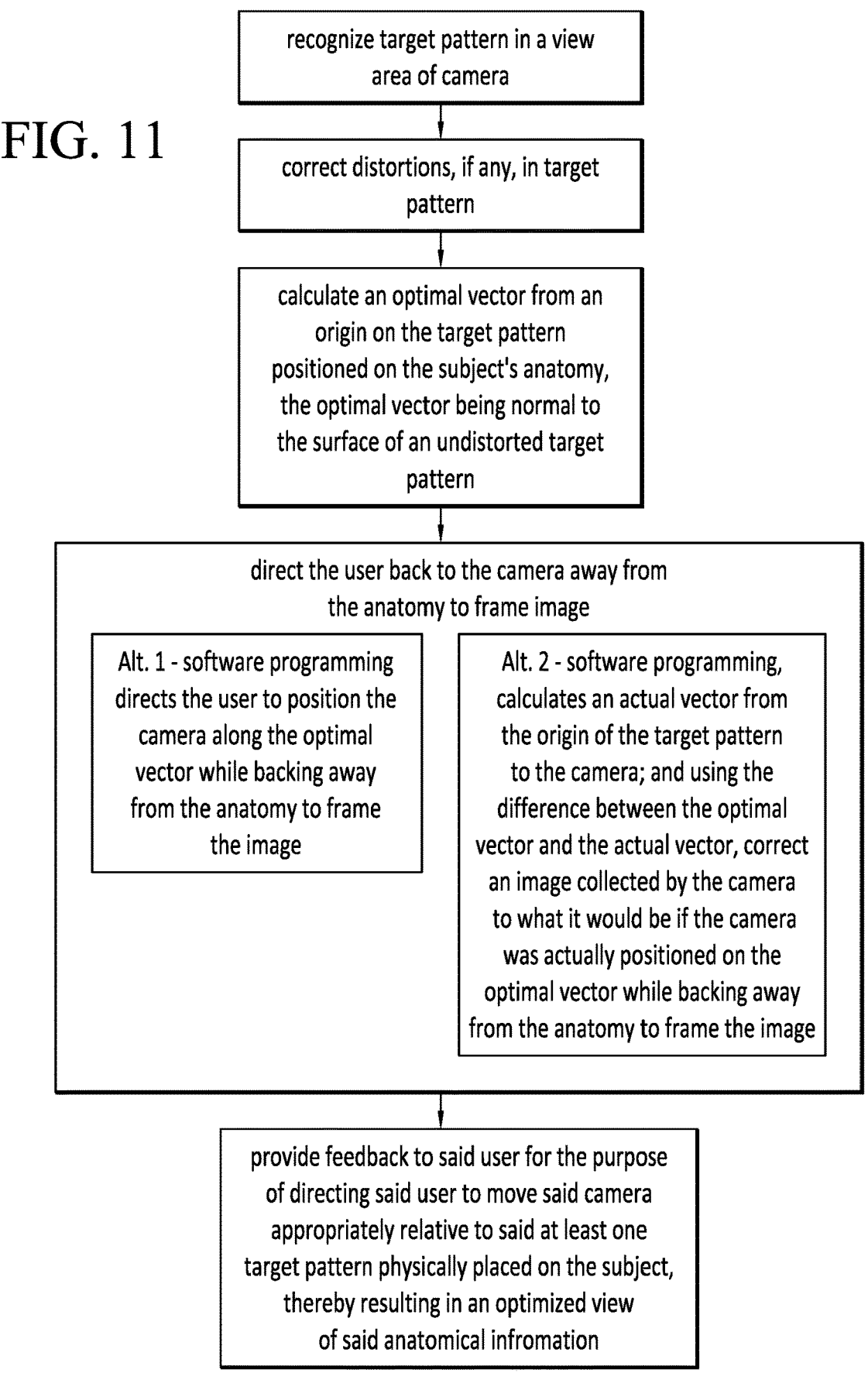
FIG. 11 illustrates the programing steps to correct distortions of the target pattern without utilizing the auto-zoom feature.

In another embodiment, distortions are corrected without the use of the auto-zoom feature. Referring now to FIG. 11, the software programming provides the following steps:

recognize the target pattern in a view area of the camera;
correct distortions, if any, in the target pattern;
calculate an optimal vector from an origin on the target pattern positioned on the subject's anatomy, the optimal vector being normal to the surface of an undistorted target pattern;

direct the user to back the camera away from the anatomy to frame the image;

provide feedback to said user for the purpose of directing said user to move said camera appropriately relative to said at least one target pattern physically placed on the subject, thereby resulting in an optimized view of said anatomical information.

There are two alternatives as to how the user is directed to back the camera away from the anatomy to frame the image. In one embodiment the software programming directs the user to position the camera along the optimal vector while backing away from the anatomy to frame the image. In an alternative embodiment the software programming, calculates an actual vector from the origin of the target pattern to the camera; and using the difference between the optimal vector and the actual vector, correct an image collected by the camera to what it would be if the camera was actually positioned on the optimal vector while backing away from the anatomy to frame the image. In yet other embodiments, the user may be directed to position the camera along the optimal vector at a different time than directing the user to back the camera away.

In another embodiment, a real target pattern is not utilized. In this embodiment, when capturing an image for the purpose of obtaining measurements, the anatomy of the patient is assessed by the end-user software program (i.e. by the App) and, prominent anatomic features, e.g. a knee center, are calculated as position references to assist in orienting the image capturing device. Use of a real target is substituted by generation of one or more virtual markers.

Anthropometric data is available for prominent anatomical features, including body segment dimensions between certain prominent anatomical features. These might include, other physical dimensions and properties of the body, measurable physical variables.

Figure 12A:
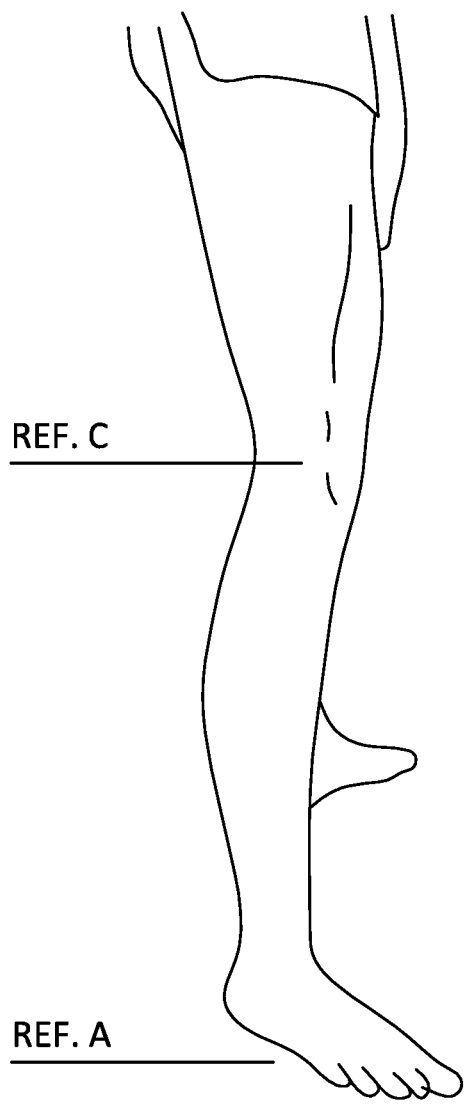
FIGS. 12A-12F illustrate the system for electronically capturing a subject's anatomy includes an auto-zoom feature, with virtual markers.
Figure 12A:
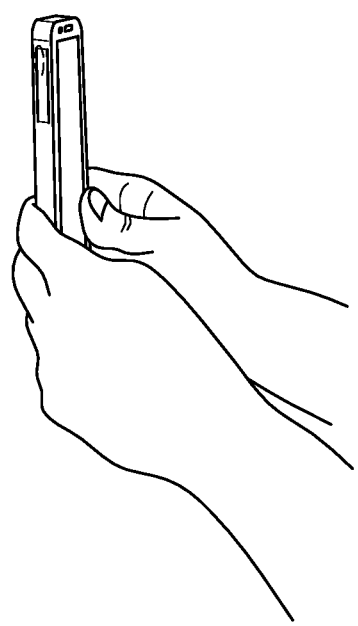
Figure 12B:
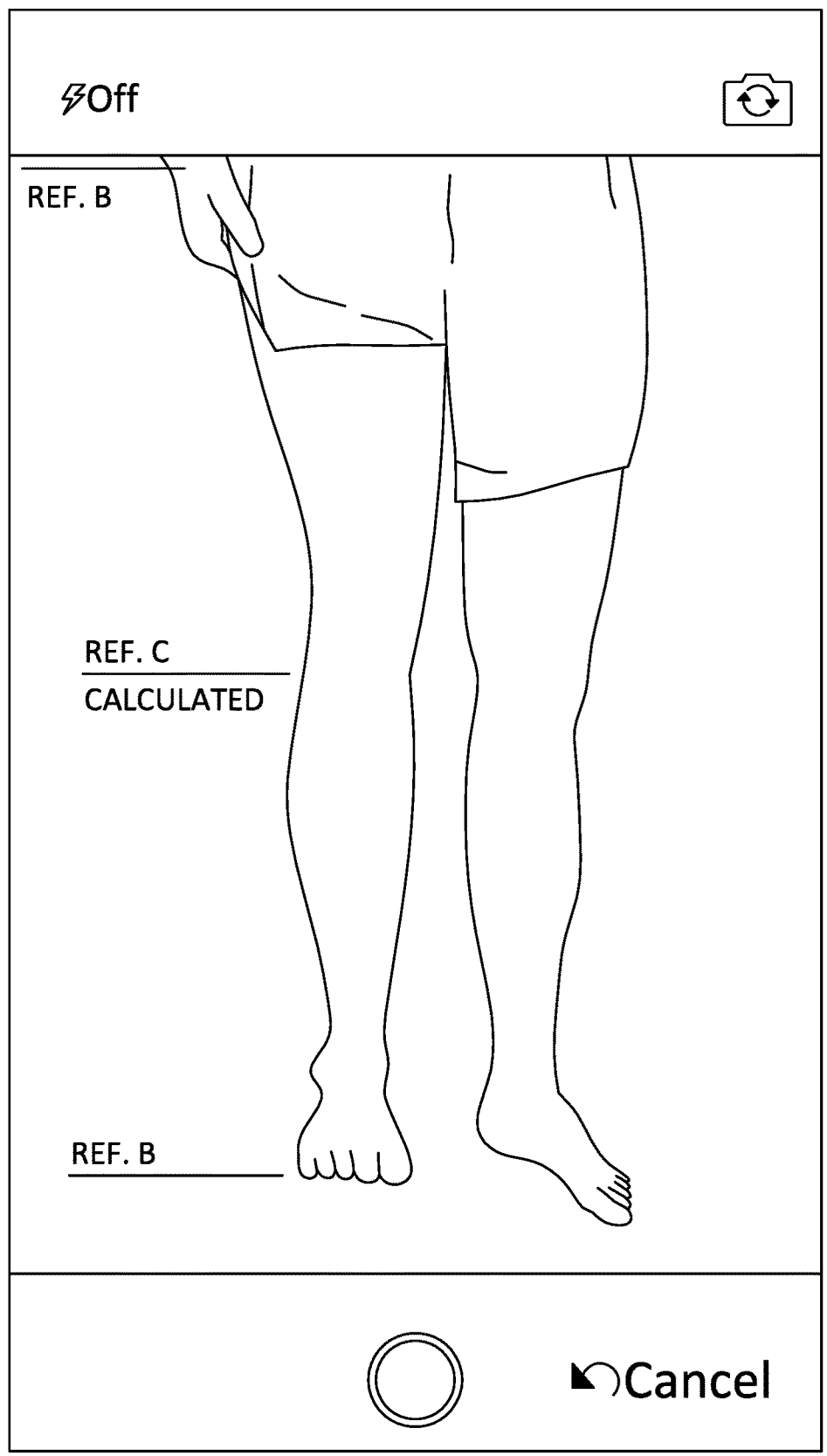

Referring now to FIGS. 12A and 12B the user positions the camera so as to recognize a subject's anatomy within the display screen. In this example, Ref. A, where the foot meets the floor is a recognized anatomical feature of the subject's anatomy which is recognized by the software. Ref. B, hip height, may be calculated from patient's height, which is provided by patient data entered by the user in conjunction with known anthropometric data. Ref. C, the knee, is calculated from stature (height) using patient data entered by the user in conjunction with known anthropometric data.

Figure 12C:
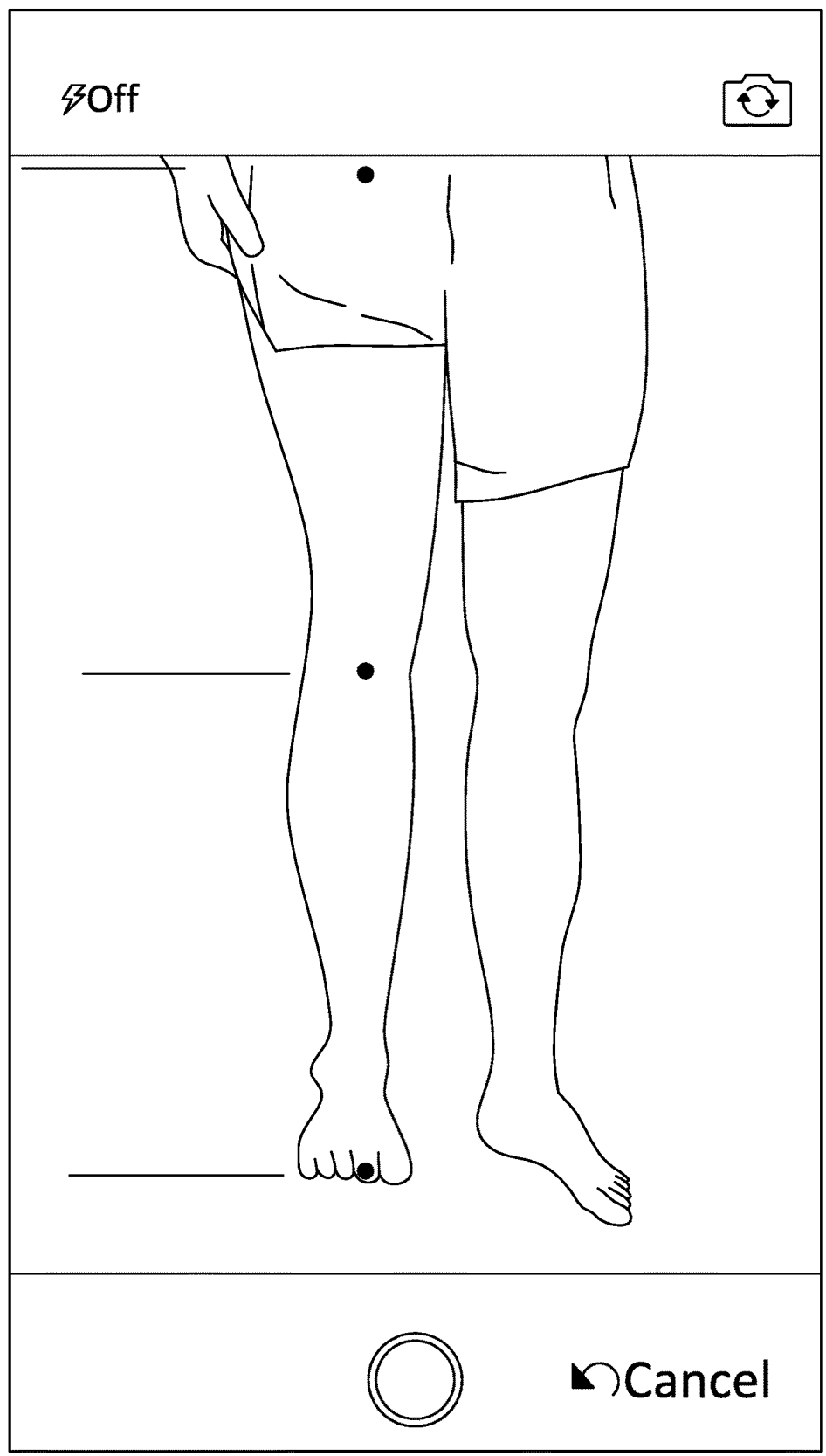
Figure 12D:
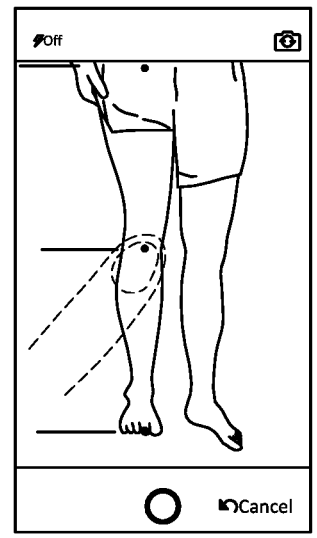

Now referring to FIG. 12C, the virtual markers are placed (i.e. "painted") on the image presented to the user on the display screen at the estimated optimal positions. As shown in FIG. 12D, in one embodiment, the user may correct placement of the three placed markers as needed using, for example, her finger tip.

Figure 12E:
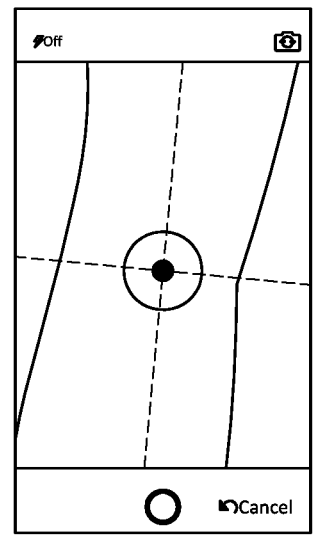

As shown in FIG. 12E, an auto-zoom feature and the virtual markers are zoomed in or out to provide proper framing of the anatomy. The auto-zoom feature is utilized while maintaining a substantially fixed camera distance from the subject. The camera provides the feedback to the user based on said anatomical features for directing the user to move the camera appropriately relative to the virtual markers, thereby resulting in an optimized view of the anatomical information. In the example shown in FIG. 12E the guidelines are canted (and typically in red) to indicate that the camera should be moved.

Figure 12F:
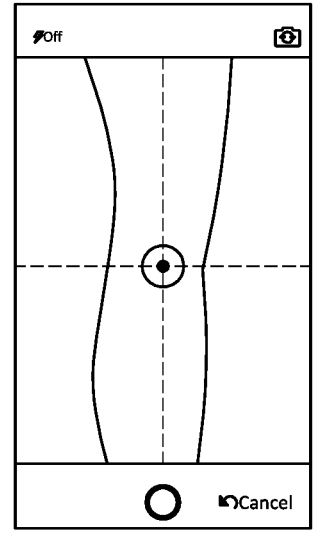

Referring now to FIG. 12F, when the pitch line and yaw line show green, the camera is positioned at the optimized view of the anatomical information of the user. The camera then captures the optimized view of the anatomical information.

With the successful anterior view complete, the end-user software program queries the user to either move the camera or the patient to take a lateral (side) view. The above steps are repeated for the lateral view process.

As discussed above, the software programming may also include an image distortion correction feature utilizing the anatomical features and position information from the camera.

In another embodiment, instead of using patient data entered by the user and known anthropometric data to estimate the optimal position of the virtual markers, the user is provided with the means to identify anatomical features of the subject's anatomy and the means to place the virtual markers to identify the anatomical features. For example, instead of the three markers shown in FIG. 12D being initially placed by the software, the three markers are put on the display and the user uses his/her finger to identify and place those markers on the three anatomical features, i.e. foot contact with floor, knee, hip.

Other embodiments and configurations may be devised without departing from the spirit of the invention and the scope of the appended claims.

The invention claimed is:

1. A system for electronically capturing a subject's anatomy, comprising:
   a) an electronic device comprising:
      i) a camera configured to capture anatomical information of the anatomy of a subject;
      ii) a display screen; and,
      iii) an end-user software program configured to interface with a user via said display screen and to process information captured on said camera; and,
   b) at least one target pattern for physical placement on the subject's anatomy;
   wherein said end-user software program comprises:
      i) a user interface to provide user control of software functions;
      ii) software programming to:
         recognize said at least one target pattern in a view area of said camera;
         utilize an auto-zoom feature to zoom in to the target pattern to provide a close-up of the target pattern, verify the target pattern, then zoom out to provide proper framing of the anatomy, wherein said auto-zoom feature is utilized while maintaining a substantially fixed camera distance from the subject; and,
         provide feedback to said user based on the size, shape, or position of said at least one target pattern, for directing said user to move said camera appropriately relative to said at least one target pattern, thereby resulting in an optimized view of said anatomical information;
      iii) means to capture the optimized view of the anatomical information via said camera.

2. The system of claim 1, wherein said electronic device is connectable to the internet, and said end-user software program is configured to transfer said captured optimized view of said anatomical information to a remote location.

3. The system of claim 1, wherein said anatomical information is used to build custom-fitted equipment to fit said subject's anatomy.

4. The system of claim 1, wherein said feedback provided to said user for directing the user to move the camera comprises feedback markers including a top distance line, a bottom distance, a pitch line, a yaw line, a center zone, and a center marker.

5. A system for electronically capturing a subject's anatomy, comprising:
 a) an electronic device comprising:
  i) a camera configured to capture anatomical information of the anatomy of a subject;
  ii) a display screen; and,
  iii) an end-user software program configured to interface with a user via said display screen and to process information captured on said camera; and,
 b) at least one target pattern for physical placement on a subject's anatomy;
 wherein said end-user software program comprises:
  i) a user interface to provide user control of software functions;
  ii) software programming to:
   recognize said at least one target pattern in a view area of said camera;
   utilize an auto-zoom feature to zoom in to the target pattern to provide a close-up of the target pattern, verify the target pattern, then zoom out to provide proper framing of the anatomy, wherein said auto-zoom feature is utilized while maintaining a substantially fixed camera distance from the subject;
   correct distortions, if any, in said at least one target pattern;
   calculate an optimal vector from an origin on the target pattern positioned on the subject's anatomy, said optimal vector being normal to the surface of an undistorted target pattern;
   calculate an actual vector from the origin of the target pattern to the camera; and
   using the difference between the optimal vector and the actual vector, correct an image collected by the camera to what it would be if the camera was actually positioned on the optimal vector, resulting in an optimized view of said anatomical information;
  iii) means to capture the optimized view of the anatomical information via said camera.

6. The system of claim 5, wherein said electronic device is connectable to the internet, and said end-user software program is configured to transfer said captured optimized view of said anatomical information to a remote location.

7. The system of claim 5, wherein said anatomical information is used to build custom-fitted equipment to fit said subject's anatomy.

8. The system of claim 5, wherein said feedback provided to said user for directing the user to move the camera comprises feedback markers including a top distance line, a bottom distance, a pitch line, a yaw line, a center zone, and a center marker.

9. A system for electronically capturing a subject's anatomy, comprising:
 a) an electronic device comprising:
  i) a camera configured to capture anatomical information of the anatomy of a subject;
  ii) a display screen; and,
  iii) an end-user software program configured to interface with a user via said display screen and to process information captured on said camera; and,
 b) at least one target pattern for physical placement on a subject's anatomy;
 wherein said end-user software program comprises:
  i) a user interface to provide user control of software functions;
  ii) software programming to:
   recognize said at least one target pattern in a view area of said camera;
   correct distortions, if any, in said at least one target pattern;
   calculate an optimal vector from an origin on the target pattern positioned on the subject's anatomy, said optimal vector being normal to the surface of an undistorted target pattern;
   direct the user to back the camera away from the anatomy to frame the image;
   provide feedback to said user for the purpose of directing said user to move said camera appropriately relative to said at least one target pattern physically placed on the subject, thereby resulting in an optimized view of said anatomical information;
  iii) means to capture the optimized view of the anatomical information via said camera.

10. The system of claim 9 wherein said software programming directs the user to position the camera along the optimal vector while backing away from the anatomy to frame the image.

11. The system of claim 9 wherein said software programming, calculates an actual vector from the origin of the target pattern to the camera; and using the difference between the optimal vector and the actual vector, correct an image collected by the camera to what it would be if the camera was actually positioned on the optimal vector while backing away from the anatomy to frame the image.

12. The system of claim 9, wherein said electronic device is connectable to the internet, and said end-user software program is configured to transfer said captured optimized view of said anatomical information to a remote location.

13. The system of claim 9, wherein said anatomical information is used to build custom-fitted equipment to fit said subject's anatomy.

14. The system of claim 9, wherein said feedback provided to said user for directing the user to move the camera comprises feedback markers including a top distance line, a bottom distance, a pitch line, a yaw line, a center zone, and a center marker.

15. A method for electronically capturing anatomical information of a subject, comprising the steps of:
 a) providing an electronic device comprising a camera, a display screen, and an end-user software program, said software program including position feedback criteria displayed on said display screen;
 b) placing a subject's anatomy and a target pattern within a view area of said camera, said target pattern being physically placed on the subject's anatomy;
 c) adjusting the position of said camera until said position feedback criteria are met, relative to said target pattern physically placed on the subject, and said end-user software program indicates to the user that said camera is in a position to provide an optimized view of anatomical information of a subject; and,
 d) capturing anatomical information;
 wherein said software program:
  utilizes an auto-zoom feature to zoom in to the target pattern to provide a close-up of the target pattern, verify the target pattern, then zoom out to provide proper framing of the anatomy, said auto-zoom feature being utilized while maintaining a substantially fixed camera distance from the subject; and,
  provides feedback to said user based on the size, shape, or position of said at least one target pattern, for directing said user to move said camera appropriately relative to said at least one target pattern, thereby resulting in an optimized view of said anatomical information.

\* \* \* \* \*